United States Patent
Han et al.

(10) Patent No.: US 6,972,189 B2
(45) Date of Patent: Dec. 6, 2005

(54) MICROORGANISM PRODUCING FRUTOSYL TRANSFERASE AND METHOD FOR PRODUCING FRUCTOOLIGOSACCHARIDES AND NEOFRUCTOOLIGOSACCHARIDES USING THE SAME

(75) Inventors: Joon Sang Han, Seoul (KR); Kang June Park, Incheon-si (KR); Dae Sub Shin, Seoul (KR); Jung Hoon Kim, Seoul (KR); Jin Chul Kim, Incheon-si (KR); Ki Chang Lee, Incheon-si (KR); Woon Hwa Lee, Seoul (KR); Seung Wook Kim, Seoul (KR); Seung Won Park, Kyuggi-do (KR)

(73) Assignee: CJ Corporation, Seoul (KR)

(*) Notice: Subject to any disclaimer, the term of this patent is extended or adjusted under 35 U.S.C. 154(b) by 0 days.

(21) Appl. No.: 10/145,256

(22) Filed: May 13, 2002

(65) Prior Publication Data

US 2003/0054499 A1 Mar. 20, 2003

(30) Foreign Application Priority Data

May 14, 2001 (KR) ........................ 2001-0026111

(51) Int. Cl.[7] ................. C12P 19/18; C12P 19/04; C12N 9/10; C12N 1/14
(52) U.S. Cl. ................ 435/97; 435/101; 435/193; 435/254.5; 435/256.3; 435/933
(58) Field of Search ................. 435/97, 101, 193, 435/256.3, 933, 254.5

(56) References Cited

U.S. PATENT DOCUMENTS

| | | | |
|---|---|---|---|
| 5,334,516 A | 8/1994 | Muramatsu et al. | 435/101 |
| 5,827,526 A | 10/1998 | Dohnalek et al. | 424/440 |
| 5,827,855 A | * 10/1998 | Kogen et al. | 514/292 |
| 6,323,021 B1 | * 11/2001 | Wang et al. | 435/254.5 |
| 2002/0015990 A1 | 2/2002 | Tomita et al. | |

FOREIGN PATENT DOCUMENTS

| | | |
|---|---|---|
| JP | 10-165192 | 6/1998 |
| JP | 11-043438 | 2/1999 |
| KR | 1989-0001127 | 4/1989 |
| KR | 2000-0057520 | 2/2002 |

OTHER PUBLICATIONS

D. Grizard and C. Barthomuf, Food Biotechnology, 12(1), 93–105, 1999.

Yun, Jong–Won et al., Korean J. Biotechnol. Bioeng. vol. 9, No. 1, 40–47, 1994.

* cited by examiner

Primary Examiner—Herbert J. Lilling
(74) Attorney, Agent, or Firm—Baker Botts L.L.P.

(57) ABSTRACT

The present invention relates to a novel microorganism and a method for producing fructooligosaccharides and neofructooligosaccharides. More particularly, the present invention relates to *Penicillium citrinum* KCTC 10225BP of soil origin which produces fructosyl transferase and hydrolyzes sucrose into fructooligosaccharides of the following formula I:

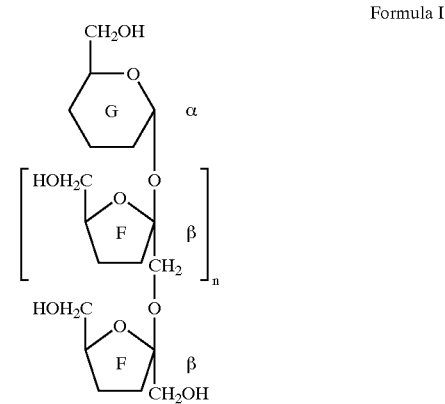

Formula I in which n is integer of 1 to 5, G represents glucose and F represents fructose, and neofructooligosaccharides of the following formula II:

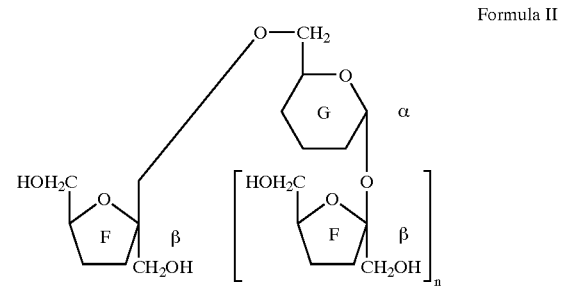

Formula II in which n is integer of 1 to 5, G and F are defined as above, at the same time using the fructosyl transferase, and to a method for producing simultaneously fructooligosaccharides and neofructooligosaccharides using said microorganism.

11 Claims, 9 Drawing Sheets

MICROORGANISM PRODUCING FRUTOSYL TRANSFERASE AND METHOD FOR PRODUCING FRUCTOOLIGOSACCHARIDES AND NEOFRUCTOOLIGOSACCHARIDES USING THE SAME

This application claims priority to Korean Patent Application Serial No. 2001-0026111, filed May 14, 2001, the contents of which are incorperated herein, in their entirety, by reference.

TECHNICAL FIELD

The present invention relates to a novel microorganism capable of simultaneously producing fructooligosaccharides and neofructooligosaccharides and to a method for producing fructooligosaccharides and neofructooligosaccharides using said microorganism. More particularly, the present invention relates to *Penicillium citrinum* KCTC 10225BP of soil origin which produces fructosyl transferase and hydrolyzes sucrose into fructooligosaccharides of the following formula I:

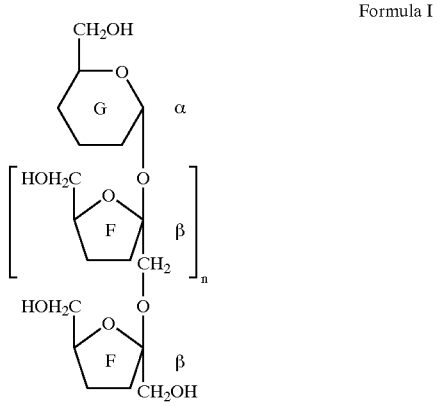

Formula I in which n is an integer of 1 to 5, G represents glucose and F represents fructose; and neofructooligosaccharides of the following formula II:

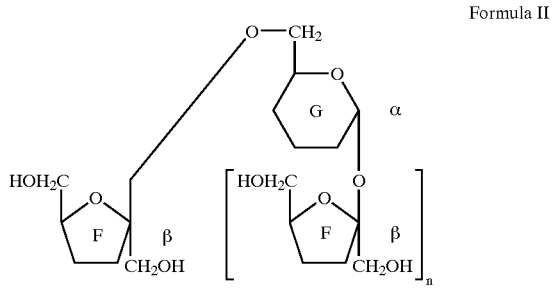

Formula II in which n is an integer of 1 to 5, G and F are defined as the above, at the same time using the fructosyl transferase, and a method for producing fructooligosaccharides and neofructooligosaccharides using said microorganism.

BACKGROUND ART

Fructooligosaccharides are a mixture of oligosaccharides including 1-Kestose (GF2), Nystose (GF3) and Fructosyl nystose (GF4), in which 1 to 3 molecule(s) of fructose are bound to sucrose by ®-(2,1) linkage, respectively and are widely contained in plants such as asparagus, onion, potato, honey, etc. They are currently spotlighted as food materials, together with oligosaccharides, due to their outstanding functions, including for example, low caloric value, promotion of proliferation of lactic acid bacteria and bifidobacteria, improvement of microflora in the intestines and inhibition of growth of pathogenic bacteria, improvement of bowel movement, and strengthening of immunity. Thus, examples of applications of oligosaccharides can be found in various industrial fields, including food, drink, confectionery, health food, and the like.

Particularly, it has been reported that the fructooligosaccharides showed excellent calcium-absorption effect when used in combination with difructose anhydride III (DFA III) (See, Japanese Patent Publication No. 11-43438). U.S. Pat. No. 5,827,526 disclosed that the duration and recurrence of diarrhea in a human can be reduced when 0.5 grams to 5 grams of fructooligosaccharides per day is administered to the patient.

Korean Patent Application Laid-Open No. 2000-57520 disclosed that a mixture of fructooligosaccharides and galactooligosaccharides with various edible ingredients may improve the flow in the bowel and effectively express prebiotic effects, as compared to other oligosaccharides. Also, currently, fructooligosaccharides are subjects of research and studies to develop diets for diabetic patients, since they are excellent in improvement of bowel movement by inducing proliferation of lactobacillus bifidus, one of the bacteria comprising normal microflora of human bowels, do not affect blood sugar levels upon ingestion, and are not decomposed by any digestive enzyme. Further, they are shown to reduce cholesterol levels in the blood and liver. Therefore, such effects of fructooligosaccharides now are not receiving careful study.

Conventionally, fructooligosaccharides have been produced by methods using microorganisms which can prepare fructosyl transferase. There are known for example, a method using the *Aureobasidium pullulans* strain, a method using *Aspergillus niger* and a method using strains of *Penicillium* and *Fusarium* sps. However, fructosyl transferase prepared by these methods has a disadvantage of a low sucrose hydrolysis titer.

Japanese Unexamined Patent Application No. 10-165192 disclosed a method for preparing ®-fructofuranosidase using *Penicillium citrinum* FERM P-15944 fungus, by which a mixture of conventional fructooligosaccharides with neofructooligosaccharides could be produced from sucrose. It is described that the neofructooligosaccharides is a mixture consisting of neokestose (6G-®-fructofuranosyl-sucrose), neonystose (6G-®-fructofuranosyl-kestose) and neofructosyl nystose (6G-®-fructofuranosyl-nystose), which have a structure in which 1 to 3 molecule(s) of fructose is (are) bound to sucrose by ®- (2,6) linkage, respectively, different from conventional fructooligosaccharides. It is also described that neofructooligosaccharides have moisturizing effects, excellent sweetness, low calories and anti-cavity effects, functions to induce proliferation of bacteria in the bowels and to promote topical immune responses in the intestinal tracts, and thus can be applicable in various fields such as sweeteners, functional foods, feed stuffs, medicines, and promoters of pesticides.

D. Grizard et al. disclosed a method for producing a mixture of fructooligosaccharides and neofructooligosaccharides using Cytolase PCL5, a commercially available enzyme derived from Aspergillus awamori (D. Grizard, C. Barthomuf, Food Biotechnology, 13 (1), 93–105, 1999).

U.S. Pat. No. 5,334,516 disclosed a method for producing neofructooligosaccharides (expressed as "branched fructooligosaccharides") with conventional fructooligosaccharides using an enzyme derived from *Aspergillus sydowi*.

Thus, the present inventors have intensively investigated and studied the prior arts and have conducted research in various ways to produce fructooligosaccharides in a high yield. As a result, we have finally identified a novel microorganism which is capable of producing fructosyl transferase having a high sucrose hydrolysis titer and confirmed that conventional fructooligosaccharides and neofructooligosaccharides could be produced in a high yield via a reaction of the microorganism with a highly concentrated sucrose solution. Based on these discoveries, the present invention has been developed.

DISCLOSURE OF THE INVENTION

It is an object of the present invention to provide a novel microorganism which can fructosyl transferase of a high titer.

It is another object of the present invention to provide a method for producing fructooligosaccharides and neofructooligosaccharides in high yield by contacting a highly concentrated sucrose solution with the microorganism.

To accomplish the above objects, the present invention provides *Penicillium citrinum* KCTC 10225BP of soil origin which produces fructosyl transferase, hydrolyzes sucrose into oligosaccharides of the following formula I:

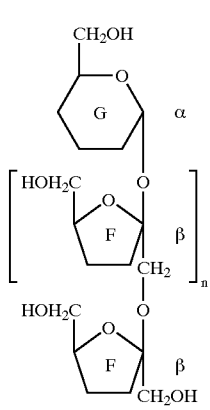

Formula I in which n is an integer of 1 to 5, G represents glucose and F represents fructose; and neofructooligosaccharides of the following formula II:

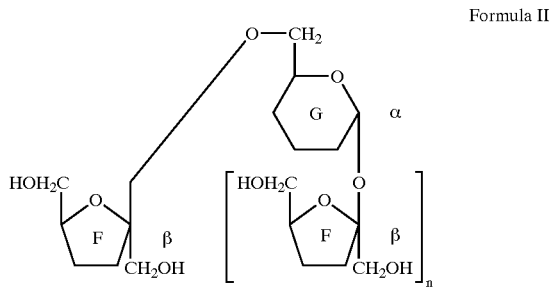

Formula II in which n is an integer of 1 to 5, G and F are defined as above, at the same time using the fructosyl transferase, and a method for producing fructooligosaccharides and neofructooligosaccharides using said microorganism.

In another aspect, the present invention provides a method for producing fructooligosaccharides and neofructooligosaccharides, the method comprising the steps of:

seed culturing the *Penicillium citrinum* KCTC 10225BP microorganism according to present invention in a first seeding medium at 26° C. to 28° C. for 2 days while agitating at a speed of 100 to 200 rpm to activate the microorganism;

mass-producing the microorganism in a fermentation medium at 26° C. to 28° C. for 72 hours while agitating at a speed of 200 to 500 rpm and injecting air at a rate of 0.5 to 1 v/vm; and collecting the produced microorganisms by centrifugation, washing them twice with 0.85% physiological saline, followed by culturing in a sucrose solution having a Brix concentration of sucrose of 60 to 77, as measured by initially inserting a sensor, at a temperature in a range of 35° C. to 50° C. and pH of 5 to 7 for 20 to 50 hours, while agitating at a speed of 100 to 300 rpm.

In yet another aspect, the present invention provides a method for producing fructooligosaccharides and neofructooligosaccharides, the method comprising the steps of:

seed culturing the *Penicillium citrinum* KCTC 10225BP microorganism according to present invention;

mass-producing the seed cultured microorganism;

mixing the mass-produced microorganisms with a carrier to form beads, which are then packed in a column; and passing a sucrose solution through the column packed with the beads.

In yet another aspect, the present invention provides fructosyl transferase derived from the *Penicillium citrinum* KCTC 10225BP microorganism according to present invention and showing a high sucrose hydrolysis titer.

BRIEF DESCRIPTION OF THE DRAWINGS

The above objects, and other features and advantages of the present invention will become more apparent after a reading of the following detailed description when taken in conjunction with the drawings, in which.

DETAILED DESCRIPTION OF THE INVENTION

Figure 1:
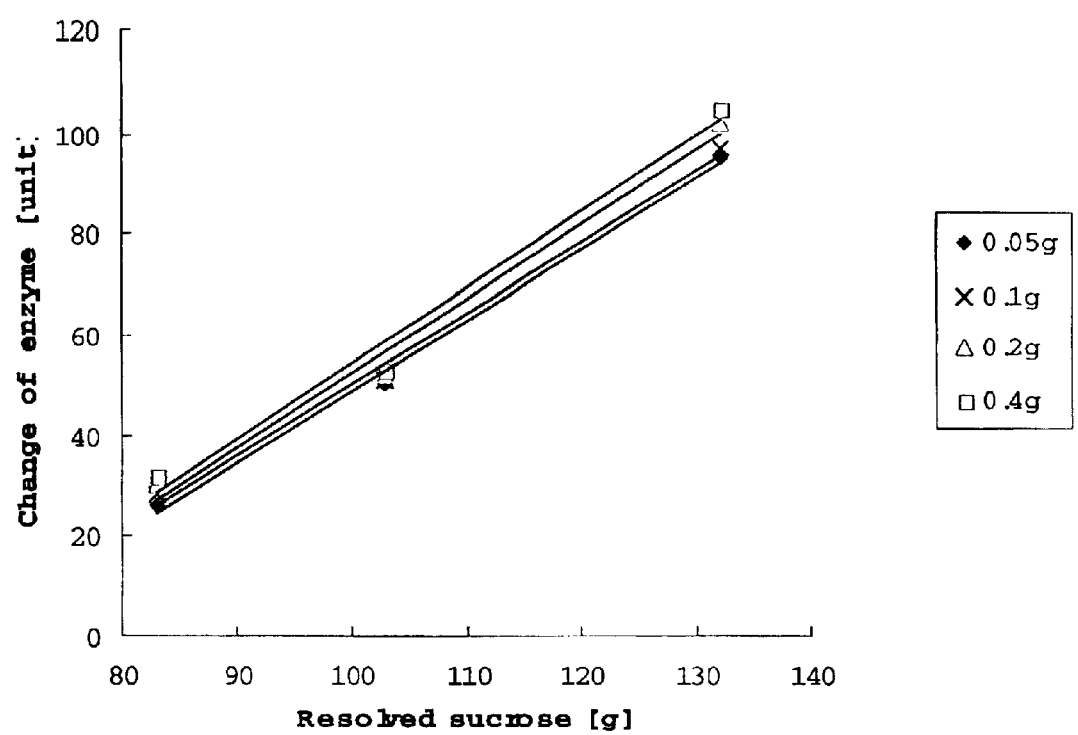
FIG. 1 is a graph showing hydrolysis levels of sucrose while varying biomass of *Penicillium citrinum* KCTC 10225BP according to the present invention, wherein the slope (unit/1 g of sucrose) is a sucrose hydrolysis titer of fructosyl transferase.

The present inventors collected soil distributed around a sugar factory located at Inchon, Korea and separated microorganisms from the soil. One of the microorganisms was found to show ability to produce fructosyl transferase of a high titer. The novel microorganism was identified as *Penicillium citrinum* which is a fungus belonging to Penicillium genus. The microorganism was deposited with Korea Research Institute of Bioscience and Biotechnology (KRIBB), located at Oun-dong, Yusong-gu, Taejon, Korea, on Feb. 27, 2001, as Deposition Access No. KCTC-10225BP, so that the microorganism can be available to a third party.

The present inventors examined scientific properties and morphologies of the *Penicillium citrinum* KCTC 10225BP microorganism according to the present invention and the results are shown in Table 2. The sucrose hydrolysis titer of fructosyl transferase prepared from the microorganism was measured. It was found to be 1.5 units/1 g of sucrose on average. Such a result demonstrates that fructosyl transferase derived from *Penicillium citrinum* KCTC 10225BP according to the present invention has a sucrose hydrolysis titer superior to any other known enzymes, considering the experimental results of U.S. Pat. No. 5,334,516, in which when hydrolyzing sucrose using an enzyme derived from *Aspergillus,* at least 5 units of the enzyme was needed to degrade 1 g of sucrose, and D. Grizard et al., in which 7 units of the enzyme derived from *Aspergillus awamori* was needed to degrade 1 g of sucrose.

By using the *Penicillium citrinum* KCTC 10225BP microorganism according to the present invention, it is possible to produce simultaneously fructooligosaccharides and neofructooligosaccharides in a high yield. Methods which can be used for the production of fructooligosaccharides and neofructooligosaccharides include batch type methods, immobilized continuous methods, etc. such as those well-known in the art.

The batch type methods are the most commonly used method, in which fructosyl transferase are reacted with a sucrose solution (substrate) by mixing microorganisms containing the enzyme with the sucrose solution to obtain a product. In an aspect, the present invention provides a batch type method for producing fructooligosaccharides and neofructooligosaccharides in a high yield using *Penicillium citrinum* KCTC 10225BP according to the present invention.

Meanwhile, the immobilized continuous methods, in which microorganisms or enzymes are immobilized in a carrier and a substrate is contacted with the carrier for reaction with the microorganisms or enzymes, have been also widely used up to now. An advantage of these methods is that microorganisms or enzymes can be reused and the reaction can be performed continuously. However, these methods also have disadvantages that for immobilization of enzymes, the enzymes contained in microorganisms should be extracted and separated and the enzymes extracted from the microorganisms are generally unstable. Therefore, currently, a method using immobilized microbial cells is used, in which microorganisms are directly immobilized in a carrier. The microbial cells-immobilized method does not require separation of the enzymes from the microbial cells and thus, can prevent the reduction of enzyme activity during the extraction of the enzymes. Also, it has an advantage that the complicated processes for extraction and separation of enzymes can be performed in a single step. Thus, in another aspect, the present invention provides a method for continuously producing fructooligosaccharides and neofructooligosaccharides by immobilizing *Penicillium citrinum* KCTC 10225BP according to the present invention in a carrier. The immobilized continuous method according to the present invention is explained in detail as follows.

First, *Penicillium citrinum* KCTC 10225BP according to the present invention is seed cultured. The seed cultured microorganism is mass-produced in a fermentation medium. The seed culturing is preferably performed at 26° C. to 28° C. for 2 days while agitating at a speed of 100 to 200 rpm. The mass production is preferably performed at 26° C. to 28° C. for 42 to 72 hours while agitating at a speed of 200 to 600 rpm and injecting air at a rate of 0.5 to 1 v/vm. The mass-produced microorganisms are then well mixed with a carrier. The mixture is formed into beads, which are then packed in a column. The carrier is preferably selected from a group consisting of alginate gel, photo cross-linked resin, acrylamide gel, |-carrageenan, chitosan and gelatin, though carriers commonly used in the art can be used without limitation. The concentration of the carrier is preferably from about 1% to about 2% (w/v). Next, a sucrose solution is passed through the column packed with the beads. Preferably, the sucrose solution has a concentration of Brix 60 to 70 and is flowed at a rate of 100 to 300 mL/hr and a temperature of 35° C. to 55° C.

Table 1 shows results of two experiments, in which fructooligosaccharides are produced by a batch type method and immobilized continuous method using *Penicillium citrinum* KCTC 10225BP according to the present invention.

TABLE 1

|  | Batch type method | Immobilized continuous method |
|---|---|---|
| Biomass of Microorganism (upon producing 100 L of fructooligo saccharides). | 400 g | 50 g |
| Production Efficiency (upon producing 100 L of fructooligo saccharides). | 0.67 L/day (100 L/150 days) | 4.02 L/day (100 L/24.9 days) |

As seen from the Table 1, when using the batch type method, 400 g of microorganisms was needed to produce 100 L of fructooligosaccharides. The reaction time required to produce 1 L of fructooligosaccharides was about 24 hours. However, after completion of the reaction, another 12 hours were required until the next reaction was begun in order to separate the produced fructooligosaccharides from the microorganisms, to wash the reaction vessel and to charge the reaction vessel with a fresh sucrose solution and microorganisms. On the contrary, in case of the immobilized continuous method, 50 g of microorganisms was needed to produce 100 L of fructooligosaccharides. The reaction time required to produce 100 L of fructooligosaccharides was about 25 days with production efficiency of 4.02 L/day. Accordingly, it was confirmed that when applying the immobilized continuous method, a smaller amount of microorganisms is needed and the production efficiency is 6 times higher, as compared to the batch type method.

Now, the present invention will be described in detail using an embodiment shown in the following examples. However, the examples are for illustration of the present invention and do not limit the scope of the present invention thereto.

EXAMPLE 1

Identification of Microorganism

Microorganisms were obtained from soil collected around a sugar factory located at Inchon, Korea. One of the microorganisms was found to show ability to produce fructosyl transferase of a high titer. The novel microorganism was identified as *Penicillium citrinum* which is a fungus belonging to Penicillium genus. The microorganism was deposited with the Korean Collection for Type Cultures (KCTC), located at Korea Research Institute of Bioscience and Biotechnology (KRIBB), #52, Oun-dong, Yusong-ku, Taejon, 305–333, Republic of Korea, on Feb. 27, 2001, as Deposition Access No. KCTC-10225BP, so that the microorganism can be available to a third party.

The microorganism *Penicillium citrinum* KCTC-10225BP according to the present invention were grown in the Czapek-Yeast Algae (CYA) medium and Malt Extract Algae (MEA), commonly used in the art for cultivation of fungi. The identified *Penicillium citrinum* KCTC 10225BP microorganism showed substantially similar properties and forms when being grown in the two media. The scientific properties and morphologies of the microorganism are shown in Table 2 below.

TABLE 2

|  | MEA medium | CYA medium |
| --- | --- | --- |
| Growth characteristics in CYA and MEA media | | |
| Growth rate (25° C. for 7 days) | 2.6 communication | 3.6 cm |
| Growth rate (37° C. for 7 days) | 2.2 cm | 2.4 cm |
| Growth rate 4° C. for 7 days) | — | — |
| Surface of Colony | Velvet-like, being flat | Velvet-like, circular with deep grooves extending outwardly |
| Mycelium | White helical hypha without conidum, forming a colony of Grey-blue-green color | White helical hypha without conidium, forming a colony of Grey-blue-green color |
| Exudates | — | — |
| Pigment | — | Forming a pale yellow pigment |
| Bottom surface of colony | Pale Yellow | Dark Yellow |
| Morphological characteristics | | |
| Conidiophores | Growing from aerial hypha Sometimes having branches of 20 to 50 μm and growing to 100 to 200 μm Smooth surface Foreign spore: furcatum-type, terminating in verticils about 2 to 4 (sometimes monoverticillate) Metulae: branched type and having 5 to 8 phialides, size: 8.6–13.8 × 2.2–3.1 μm Phialide: ampulliform, size: 4.3–8.3 × 1.8–2.9 | |
| Conidia | Size: 2.4–3.2 × 2.0–3.1 μm Spherical Growing in a column shape unwound at the ends of conidia | |

EXAMPLE 2

Seed Cultivation and Measurement of Enzyme Titer

As a medium for use in the seed cultivation of the *Penicillium citrinum* KCTC 10225BP microorganism, a modification of the medium composition used in culturing the fructooligosaccharides-producing microorganism, as described in Korean Laid-open publication No. 1989-1127, was used. The modified composition is shown in Table 3 below. The microorganism was cultured in a 250 mL flask and the added amount of the medium was 50 mL. The culturing was performed in a agitating incubator with an agitation speed of 150 rpm at 28° C. for 2 days.

TABLE 3

| Ingredients | Composition (g/L) |
| --- | --- |
| Sucrose | 200 |
| NaNo$_3$ | 2 |
| K$_2$HPO$_4$ | 5 |
| Yeast extract | 20 |
| MgSO$_4$ 7H$_2$O | 1 |
| KCl | 1 |

Note:
pH corrected to 6.0 with 5N HCl

Next, the sucrose hydrolysis titer of fructosyl transferase which was prepared from the cultured *Penicillium citrinum* KCTC 10225BP was measured. The sucrose hydrolysis titer was measured according to the method described by Shinohara Satoshi (Japanese Unexamined Patent Application No. 10-165192). The enzyme titer was defined as an amount (μmol) of glucose produced by hydrolysis of sucrose, a sugar substrate, per unit time (minute). The fructosyl transferase prepared from the microorganism *Penicillium citrinum* KCTC 10225BP according to the present invention was found to have a sucrose hydrolysis titer of 1.5 unit/1 g of sucrose on an average. Such a result demonstrates that fructosyl transferase derived from *Penicillium citrinum* KCTC 10225BP according to the present invention has a sucrose hydrolysis titer superior to any other known enzymes, considering the experimental results of U.S. Pat. No. 5,334,516, in which when hydrolyzing sucrose using an enzyme derived from *Aspergillus*, at least 5 units of the enzyme was needed to degrade 1 g of sucrose, and D. Grizard et al., in which 7 units of the enzyme derived from *Aspergillus awamori* was needed to degrade 1 g of sucrose.

Also, upon examination of the sucrose hydrolysis titer according to the biomass of the microorganisms, it was noted that as the biomass of *Penicillium citrinum* KCTC 10225BP increases, degradation of sucrose is increased.

EXAMPLE 3

Main Cultivation

Figure 2A:
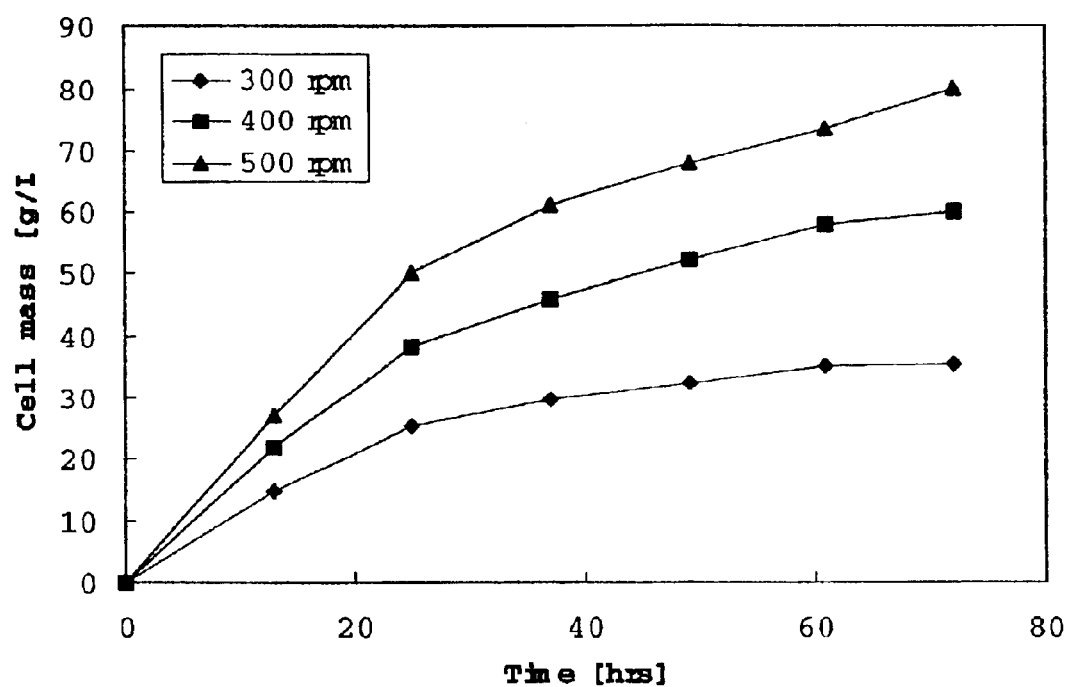
FIG. 2a is a graph showing the change in biomass of microorganisms according to the fermentation time of the main cultivation using a fermentor, while varying the agitation speed from 300 rpm to 500 rpm.
Figure 2B:
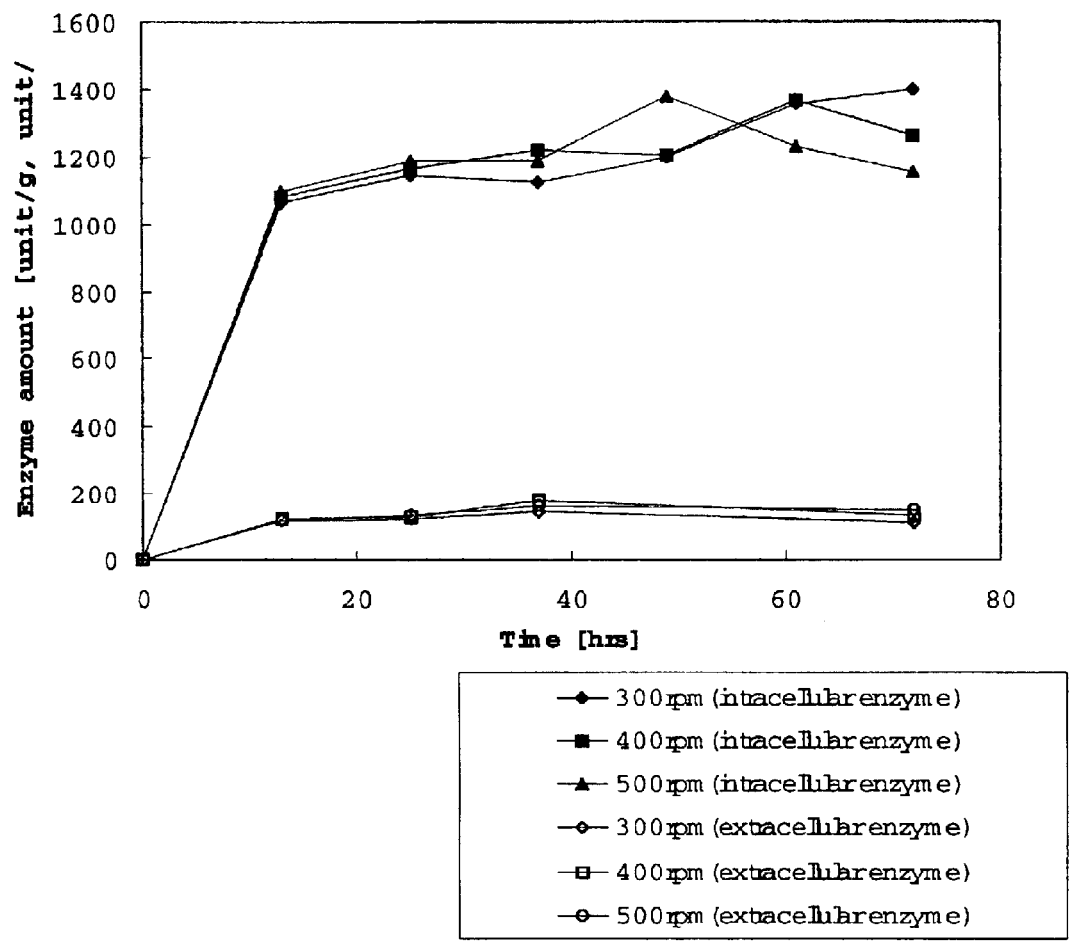
FIG. 2b is a graph showing the change in the amount of intracellular and extracellular enzymes according to the fermentation time of the main cultivation using a fermentor, while varying the agitation speed from 300 rpm to 500 rpm.
Figure 2C:
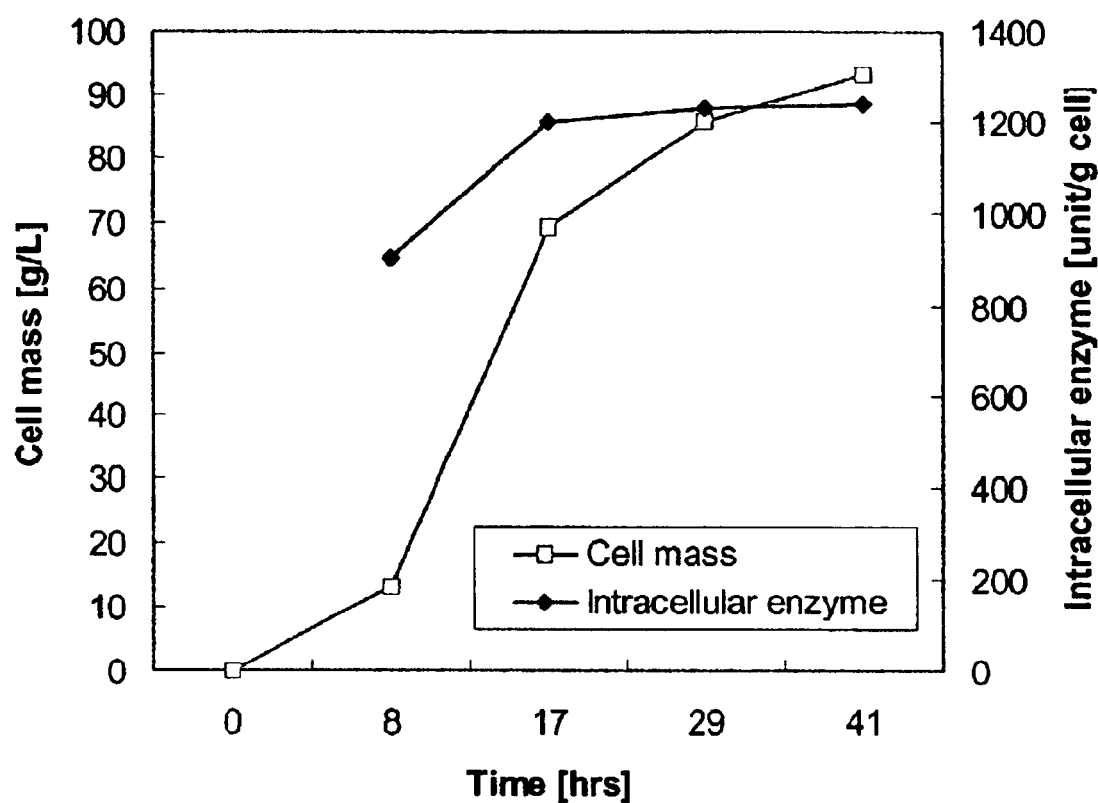
FIG. 2c is a graph showing the change in biomass of the microorganisms and the amount of intracellular enzymes according to the fermentation time of the main cultivation using a fermentor at the agitation speed of 600 rpm.

The main cultivation (mass-production) was performed in a 5 L fermentor (Hanil R&D Co., Ltd. Korea) using the microorganism seed cultured in Example 2. The microorganism was inoculated in an amount of 5% (v/v) of the medium in the fermentor. The reaction conditions were a modification of method described by Yu Moo-Young (Korean laid-open Publication No. 1989-01127). FIG. 2a shows the change in biomass of microorganisms according to the cultivation period upon varying the agitation speed of the agitator in the fermentor from 300 rpm to 500 rpm. As can be seen in FIG. 2a, as the agitation speed was raised, the amount of the microorganisms increased. FIG. 2b shows the change in the amount of intracellular and extracellular enzymes according the agitation speed. At the agitation speed of 500 rpm, the amount of intracellular enzymes showed a tendency to decrease after 50 hours. It was believed that this was caused by aging of the microorganisms and deterioration of the environment in the fermentor. Similarly, at the agitation speed of 400 rpm, the amount of intracellular enzyme was reduced after 50 hours. However, no increase of the amount of extracellular enzyme was observed. The increase of the amount of extracellular enzyme due to secretion by the microorganism was expected to be about 20 units, considering the volume of the fermentor, which was too tiny to be detected. FIG. 2c shows the change in biomass of the microorganisms and the amount of intracellular enzymes according to the fermentation time of the main cultivation using a fermentor at the agitation speed of 600 rpm. Over the culturing time, the biomass of the microorganisms and the amount of the enzyme increased. When increasing the agitation speed of the fermentor, the biomass of the microorganisms showed a tendency to increase. With respect to the morphology, micro-colloids were observed at an agitation speed of 400 rpm or more, and large pellets having a diameter of 2 were observed at an agitation speed of 200 rpm or less.

In terms of enzyme production, the amount of the enzyme present in the microorganisms was 1400 units per 1 g of microorganism, and the amount of the enzyme existing outside of the microorganisms was 150 units per 1 mL of the culturing medium. Therefore, it was shown that the microorganism according to the present invention produced 2.8 times more enzyme than the *Penicillium citrinum* FERM P-15944 of Shinohara et al. (Japanese Unexamined Patent Application No 10-165192), which contains the enzyme in an amount of 500 unit/g.

EXAMPLE 4

Production of Fructooligosaccharides Using a Batch Type Method

Fructooligosaccharides were produced by reacting the microorganisms prepared in Example 2 with a sucrose solution. The total fructooligosaccharides contents (solid %) was calculated by division with the sum of the produced conventional fructooligosaccharides, neofructooligosaccharides, fructose, glucose and remained sucrose.

Figure 3A:
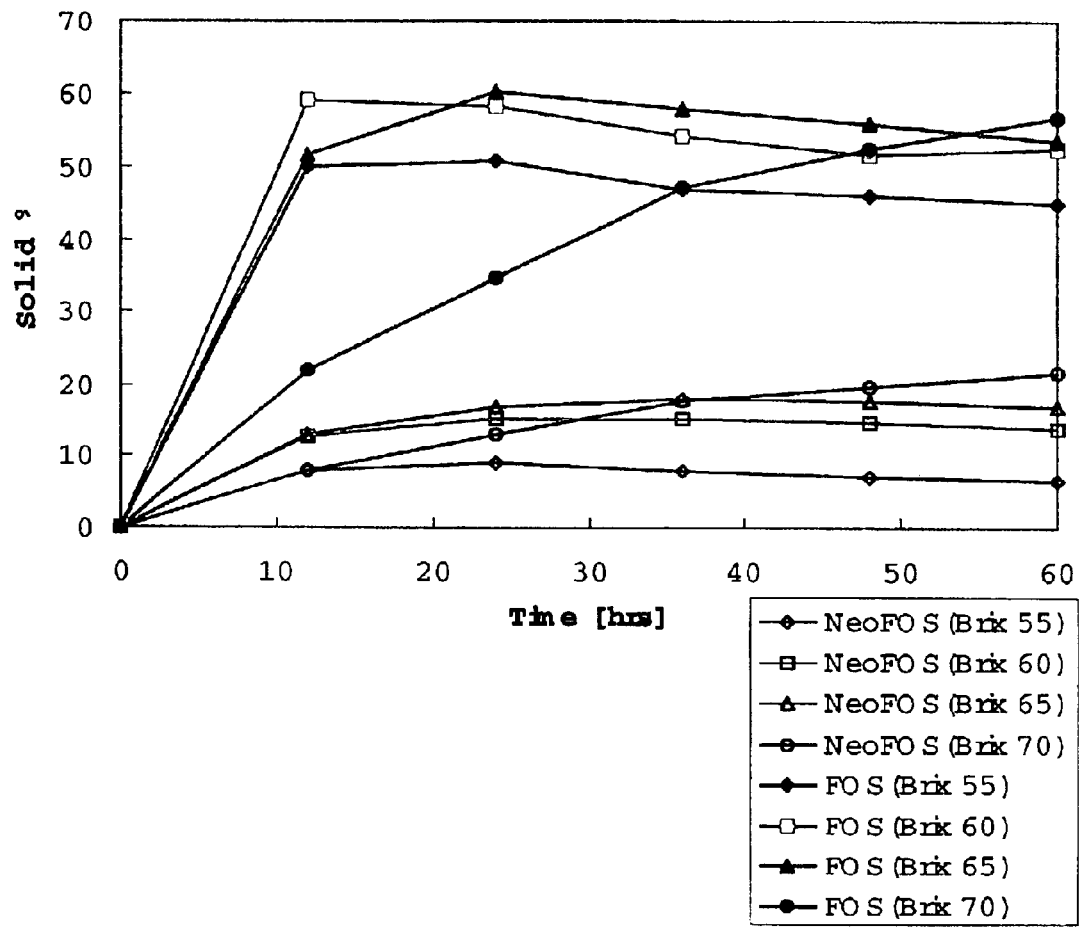
FIG. 3a is a graph showing the change in the amount of produced fructooligosaccharides and neofructooligosaccharides according to the concentration of sucrose in a batch type fermentation after inoculation of *Penicillium citrinum* KCTC 10225BP according to the present invention into 3 of a sucrose solution in a 5 fermentor.

The change of the total fructooligosaccharides contents (solid %) were measured according to the agitation speed, culturing time, sucrose concentration, pH and temperature change. In FIG. 3a, the change in the amount of produced total fructooligosaccharides according to the concentration of sucrose is shown. The highest production yield of the oligosaccharides was observed at a sucrose concentration of Brix 60 to 70. When the concentration of sucrose was higher than Brix 70, sucrose was crystallized as white precipitates, which interfered with the reaction with fructooligosaccharides. Therefore, the optimal concentration of sucrose for industrial production is up to Brix 70. Meanwhile, with a low concentration of sucrose, the reaction can be contaminated by other microorganisms. Accordingly, it was found that the optimal concentration of sucrose was Brix 65 to 70. In terms of the reaction time, in 24 hours, the solid ratio reached the maximum of 65%, which suggested that the present invention can be applied to practical industrial production without problems.

Figure 3B:
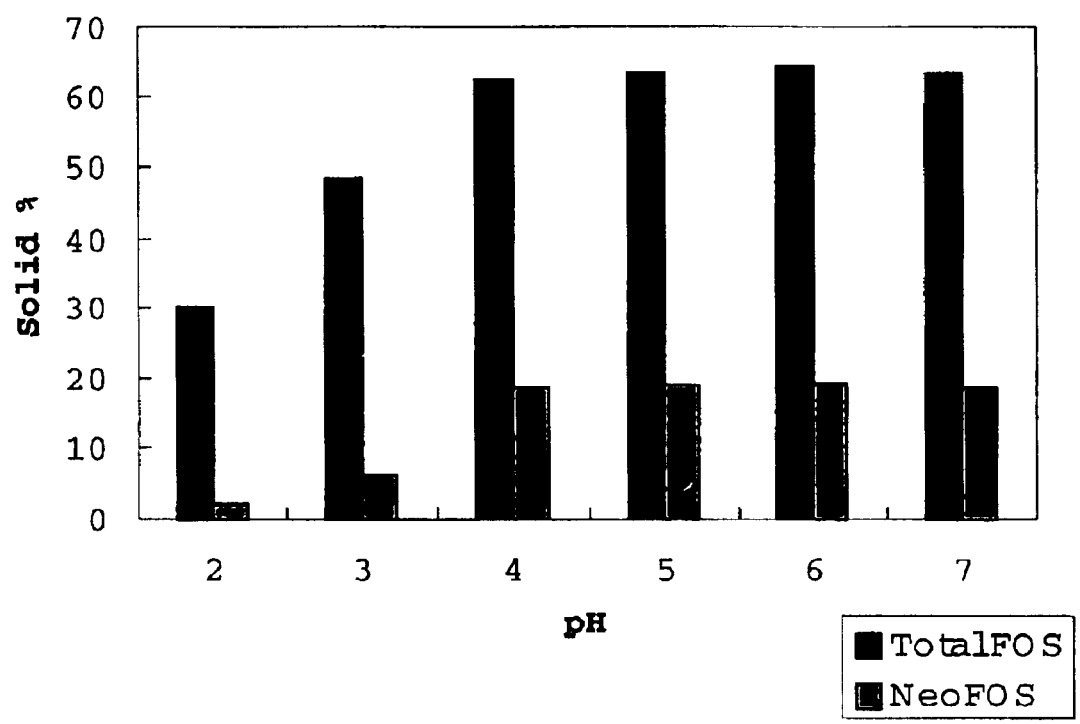
FIG. 3b is a graph showing the change in the amount of produced fructooligosaccharides and neofructooligosaccharides according to the hydrogen ion concentration (pH) in a batch type production after mixing of biomass of *Penicillium citrinum* KCTC 10225BP according to the present invention into 3 of a sucrose solution in a 5 reactor.

FIG. 3b shows the change of the fructooligosaccharides contents (solid %) according to the present invention at pH ranging from 3 to 7. It was noted that at pH 5 to 7, the production yield of fructooligosaccharides is high.

In the subsequent experiments, the sucrose solution was subjected to reaction without adjusting the pH of the reaction by addition of a separate buffer solution. Therefore, the method for producing neofructooligosaccharides can be further simplified without an additional treatment, in terms of industrial production.

Figure 3C:
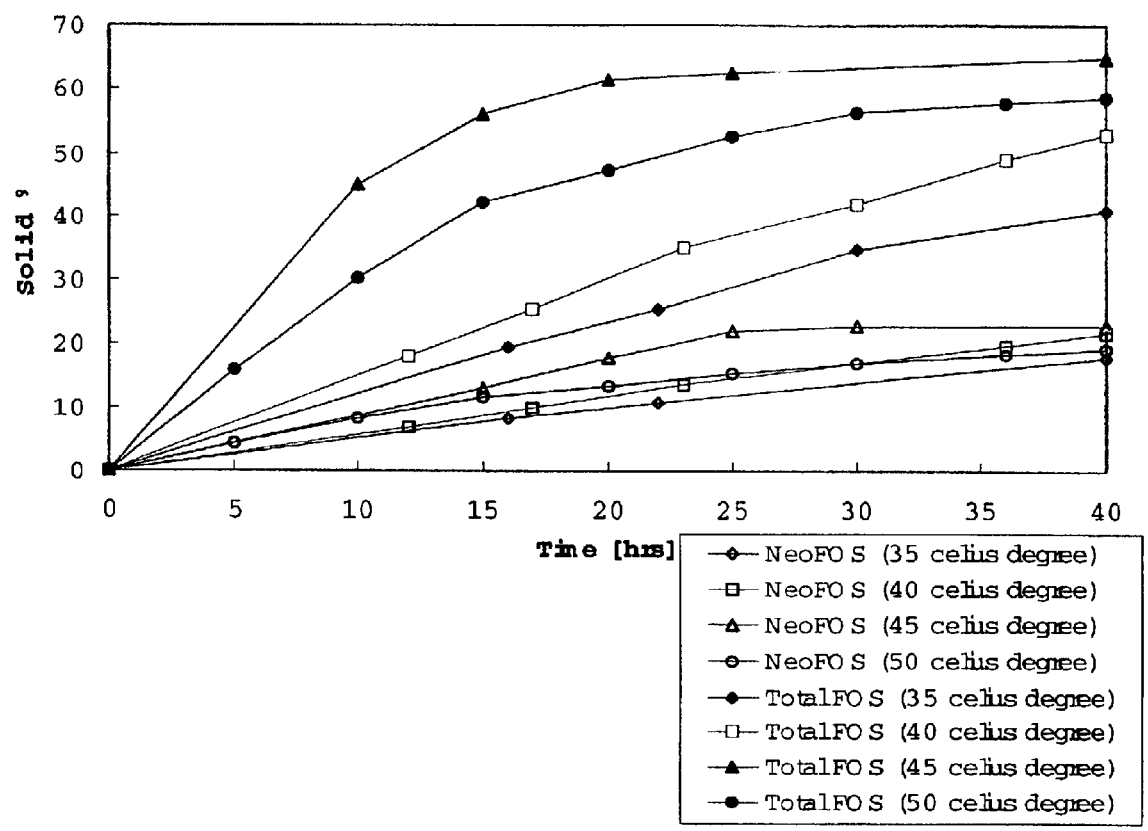
FIG. 3c is a graph showing the change in the amount of produced fructooligosaccharides and neofructooligosaccharides according to temperature in a batch type production after mixing of biomass of *Penicillium citrinum* KCTC 10225BP according to the present invention into 3 of a sucrose solution in a 5 reactor.

FIG. 3c shows the change in the total fructooligosaccharides contents (solid %) according to the reaction temperature. The total fructooligosaccharides contents showed a tendency to constantly increase up to 40° C. The highest reactivity was observed at 45° C. in terms of the reaction rate. The reaction was shown to be completed in 24 hours. It is expected that the problems associated with contamination by other microorganisms could be solved since the cultivation was performed at a high temperature. However, the total amount of the produced fructooligosaccharides was not significantly higher, although the enzyme titer at 45° C. was greater than those disclosed in other documents. This can be explained by a theory which has been proposed, stating that production of oligosaccharides is inhibited by accumulation of glucose produced by hydrolysis of sucrose in the reactor.

As a solution for this, methods for consuming glucose have been suggested, which include for example, a method for consuming glucose by addition of glucose oxidase or yeast (See, Yoon, Jong-won, et al., The Bulletin of the Korean Society for Biotechnology and Bioengineering, 9, 40–47, 1994). However, in the present invention, such method was not employed, since impurities could be produced.

Figure 3D:
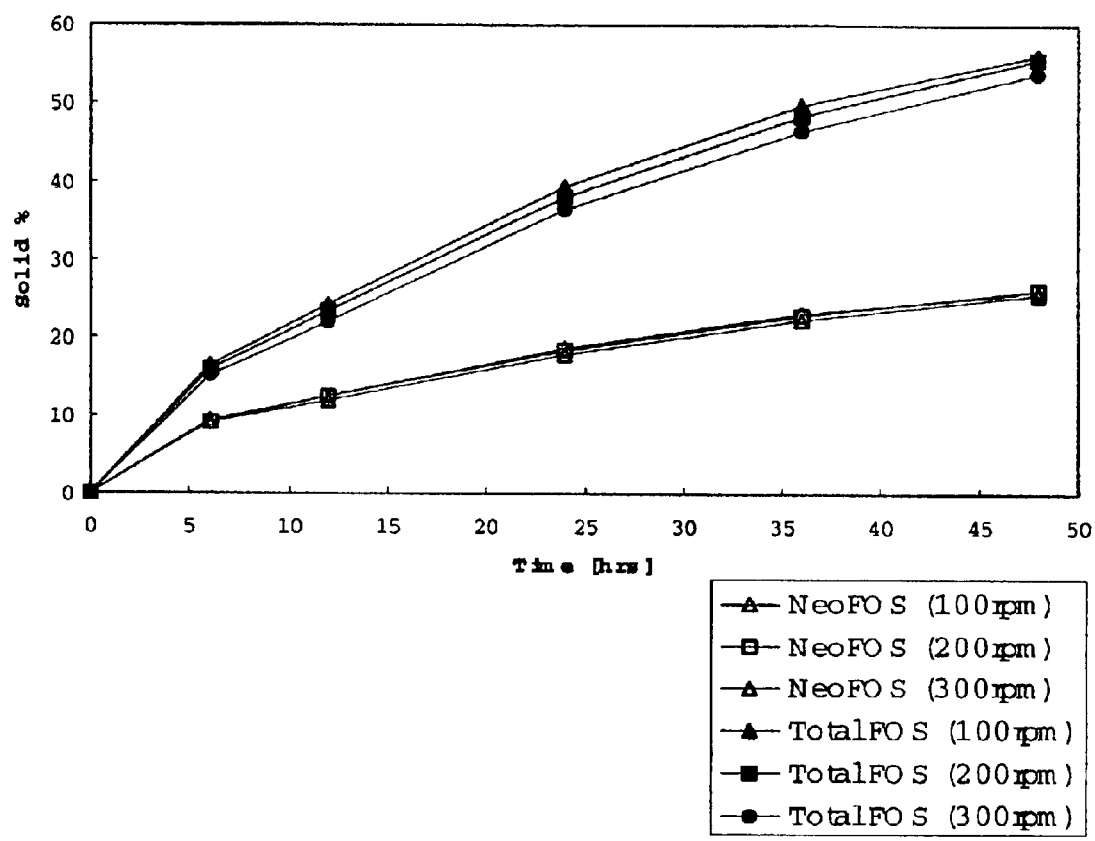
FIG. 3d is a graph showing the change in the amount of produced fructooligosaccharides and neofructooligosaccharides according to the agitation speed in a batch type production after mixing of biomass of *Penicillium citrinum* KCTC 10225BP according to the present invention into 3 of a sucrose solution in a 5 reactor.

FIG. 3d shows the change of the total fructooligosaccharides contents (solid %) according to the agitation speed. It was noted that the reactivity decreased as the agitation speed increased. It is believed that the reaction area between the microorganisms and the sucrose solution was decreased by bubbles generated when the agitator rotated at a high speed. Therefore, it was noted that the optimal agitation speed is up to 200 rpm. In the present invention, 100 rpm was used for production of fructooligosaccharides. As a consequence of performing the above-described experiments for production of fructooligosaccharides containing neofructooligosaccharides, the optimal conditions for producing fructooligosaccharides are defined as a sucrose concentration of Brix 60 to 65, a reaction temperature of 45° C., a reaction time of 24 hours and an agitation speed of 100 rpm.

EXAMPLE 5

Continuous Production of Fructooligosaccharides Via Immobilization of Microorganism

Figure 4:
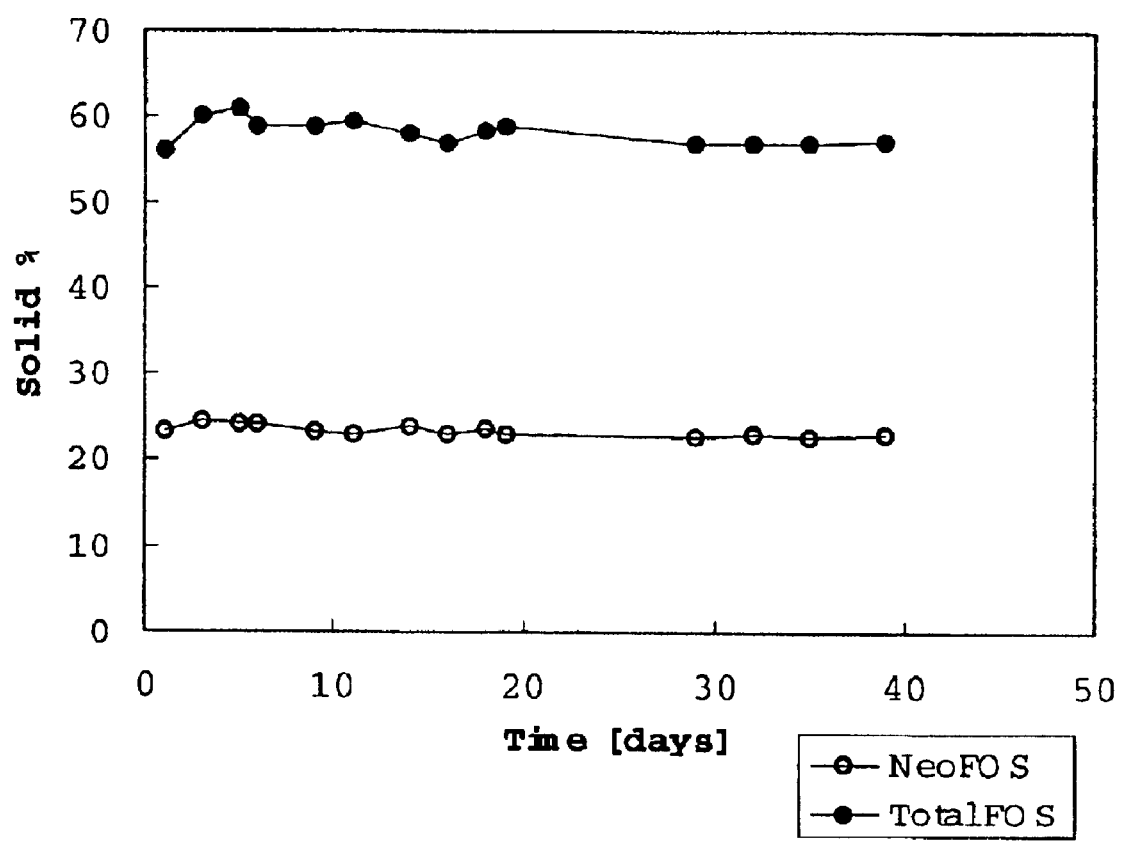
FIG. 4 is a graph showing the change in the amount of produced fructooligosaccharides and neofructooligosaccharides when *Penicillium citrinum* KCTC 10225BP according to the present invention which has been fixed in alginate is continuously reacted with highly concentrated sucrose solution.

*Penicillium citrinum* KCTC 10225BP seed cultured in Example 2 was inoculated in an amount of 5% (v/v) of medium and cultivated in a 5 L fermentor (Hanil R&D Co., Ltd. Korea). After completion of the cultivation, the microorganisms were collected and immobilized in sodium alginate (Junsei Chemical, Japan) to produce fructooligosaccharides. The microorganisms at a certain concentration were mixed with the alginate at a certain concentration. The resulting mixture was flowed at a predetermined rate using a peristaltic pump (Gilson, France) and dropped through a needle having a diameter of 1 mm at a height of 20 cm to 1% aqueous calcium chloride ($CaCl_2$) solution, being stirred using a magnet stirrer. The 1% aqueous calcium chloride ($CaCl_2$) solution was used to form beads via ion exchange reaction between calcium ions ($Ca^{2+}$) in the solution and sodium ions ($Na^+$) of the alginate. In order to determine the optimal concentrations of microorganisms and the alginate to be combined, microorganisms at a concentration of 25 to 100 g/were mixed with the alginate at a concentration of 1% to 2%. As a result, it was found that when microorganisms at a concentration up to 50 g/L were mixed with the alginate at a concentration up to 1.5%, perfectly spherical beads were formed. Over the foregoing concentrations, beads of non-uniform shapes were formed due to increase of viscosity. Therefore, in this example, microorganisms at a concentration of 50 g/L were mixed with the alginate at a concentration of 1.5% to produce beads. The resulting beads were stored at 4° C. for 10 hours, washed with distilled water and dipped in a sucrose solution of Brix 60 at 4° C. for 10 hours for aging. Then, the beads were packed in a 1 L glass column and a sucrose solution of Brix 60 were flowed through the column. Here, the reaction temperature was 45° C. and the sucrose solution was injected at a rate of 200 mL/hour by a peristaltic pump. FIG. 4 shows the change in the amount of fructooligosaccharides and neofructooligosaccharides produced from the immobilized continuous method for 40 days. It was noted that solid contents of the total produced fructooligosaccharides (%) were constant within a range of 55% to 60% and both shape and hardness of beads were not different from the initial stage.

As a consequence of performing the above-described experiments for production of fructooligosaccharides containing neofructooligosaccharides, the optimal conditions for producing fructooligosaccharides by the immobilized continuous method were found as a sucrose concentration of Brix 60, a reaction temperature of 45° C., and a flow rate of the sucrose solution of 150 to 200 mL/hour.

EXAMPLE 6

Analysis of Fructooligosaccharides

The fructooligosaccharides obtained from Example 4 and Example 5 were analyzed using a high-performance liquid chromatography (HPLC) system (Shimadzu, Japan). A ODS column (5 μm, 150 mm×4 mm) produced by Daiso Co., Ltd. (Osaka, Japan) and a refractive index detector were used. Since there was detected a substance different from the conventional fructooligosaccharides, the products were separated using a genuine preparative high-performance liquid chromatography (Prep-HPLC) system produced by Waters Corp. (Massachusetts, USA). The resulting fractions were subjected to a NMR analysis using an ARX 400 MHz NMR spectrometer (Bruker, Germany) to determine their structure. Results are shown in Table 4 below.

TABLE 4

| Kestose | | Neo Kestose | | Nystose | | Neo Nystose | |
|---|---|---|---|---|---|---|---|
| Component | δC | Component | δC | Component | δC | Component | δC |
| $^1F_1$ 1 | 63.7 | $^6F_1$ 1 | 63.00 | $^1F_1$ 1 | 63.82 | $^1F_1$ 1 | 62.99 |
| 2 | 106.7 | 2 | 106.41 | 2 | 106.0 | 2 | 106.36 |
| 3 | 79.4 | 3 | 79.58 | 3 | 79.6 | 3 | 79.58 |
| 4 | 76.6 | 4 | 77.13 | 4 | 76.6 | 4 | 77.10 |
| 5 | 84.0 | 5 | 83.86 | 5 | 84.0 | 5 | 83.82 |
| 6 | 65.0 | 6 | 65.08 | 6 | 64.98 | 6 | 65.03 |
| $^1F_2$ 1 | 63.2 | $^1F_1$ 1 | 64.25 | $^1F_2$ 1 | 63.63 | $^1F_2$ 1 | 63.77 |
| 2 | 106.5 | 2 | 106.43 | 2 | 105.8 | 2 | 105.97 |
| 3 | 79.4 | 3 | 79.04 | 3 | 80.3 | 3 | 79.19 |
| 4 | 77.2 | 4 | 76.70 | 4 | 77.2 | 4 | 76.52 |
| 5 | 83.9 | 5 | 84.06 | 5 | 83.8 | 5 | 83.91 |
| 6 | 65.1 | 6 | 65.12 | 6 | 65.04 | 6 | 64.90 |
| G 1 | 95.3 | G 1 | 94.72 | $^1F_3$ 1 | 63.16 | $^1F_3$ 1 | 63.17 |
| 2 | 73.9 | 2 | 73.73 | 2 | 106.4 | 2 | 106.42 |
| 3 | 75.4 | 3 | 75.17 | 3 | 79.5 | 3 | 79.36 |
| 4 | 72.0 | 4 | 71.94 | 4 | 77.1 | 4 | 77.20 |
| 5 | 75.20 | 5 | 74.26 | 5 | 83.8 | 5 | 83.82 |
| 6 | 62.9 | 6 | 63.08 | 6 | 65.03 | 6 | 65.03 |
| | | | | G 1 | 95.3 | G 1 | 94.97 |
| | | | | 2 | 73.9 | 2 | 73.75 |
| | | | | 3 | 75.4 | 3 | 75.26 |
| | | | | 4 | 72.0 | 4 | 71.90 |
| | | | | 5 | 75.2 | 5 | 74.27 |
| | | | | 6 | 62.89 | 6 | 63.03 |

As shown in the above table, it was confirmed that the fructooligosaccharides produced using *Penicilliun citrinum* KCTC 10225BP microorganism according to the present invention contained conventional fructooligosaccharides (formula I) and also neofructooligosaccharides (formula II) having a structure different from that of the conventional fructooligosaccharides. Therefore, it was proven that the *Penicillium citrinum* KCTC 10225BP microorganism used in the present invention can produce conventional fructooligosaccharides simultaneously with neofructooligosaccharides having a different structure.

INDUSTRIAL APPLICABILITY

As described above, the present inventors identified a novel microorganism, *Penicillium citrinum* KCTC 10225BP, which can hydrolyze sucrose into the conventional fructooligosaccharides and neofructooligosaccharides. Fructosyl transferase prepared from the *Penicillium citrinum* KCTC 10225BP has a sucrose hydrolysis titer much higher than the conventional microorganism-derived enzymes Therefore, by using *Penicillium citrinum* KCTC 10225BP, it is possible to produce fructooligosaccharides along with neofructooligosaccharides in a high yield at a low cost.

What is claimed is:

1. An isolated and purified culture of *Penicillium citrinum* KCTC 10225BP having a fructosyl transferase that hydrolyzes sucrose into fructooligosaccharides of the following formula I:

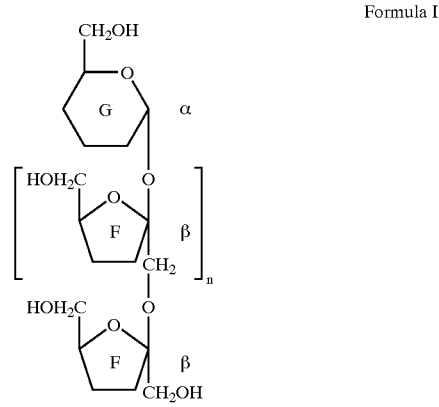

Formula I in which n is an integer of 1 to 5, G represents glucose and F represents fructose, and neofructooligosaccharides of the following formula II:

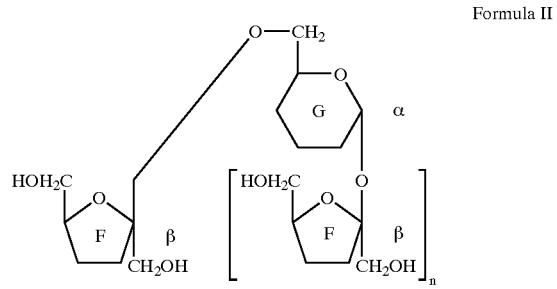

Formula II in which n is an integer of 1 to 5, G represents glucose and F represents fructose, using said fructosyl transferase.

2. A method for producing fructooligosaccharides and neofructooligosaccharides comprising contacting sucrose with a purified and isolated *Penicillium citrinum* KCTC 10225BP having a fructosyl transferase that hydrolyzes sucrose into fructooligosaccharides of the following formula I:

Formula I

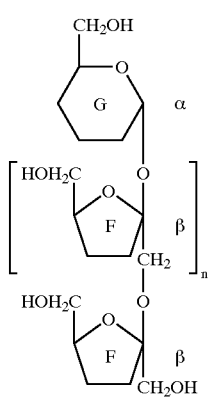

in which n is an integer of 1 to 5, G represents glucose and F represents fructose, and neofructooligosaccharides of the following formula II:

Formula II

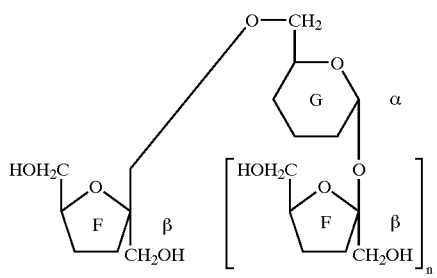

in which n is an integer of 1 to 5, G represents glucose and F represents fructose, using said fructosyl transferase.

3. A method for producing fructooligosaccharides and neofructooligosaccharides comprising:

seed culturing in a first medium at 26° C. to 28° C. for 2 days while agitating at a speed of 100 to 200 rpm a *Penicillium citrinum* KCTC 10225BP having a fructosyl transferase that hydrolyzes sucrose into fructooligosaccharides of the following formula I:

Formula I

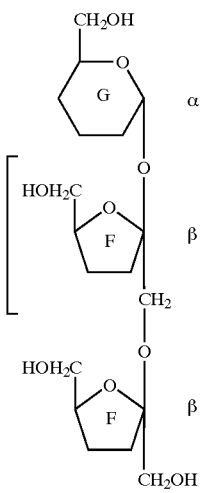

in which n is an integer of 1 to 5, G represents glucose and F represents fructose, and neofructooligosaccharides of the following formula II:

Formula II

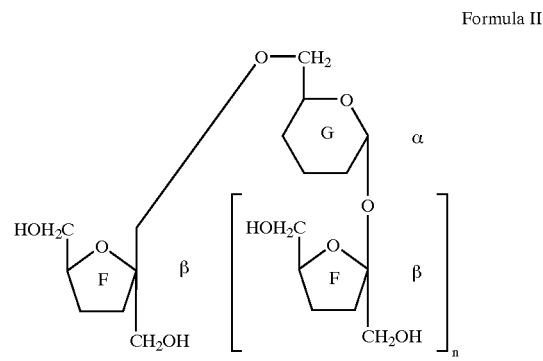

in which n is an integer of 1 to 5, G represents glucose and F represents fructose, using said fructosyl transferase;

mass-producing said microorganism in a fermentation medium at 26° C. to 28° C. for 72 hours while agitating at a speed of 200 to 600 rpm and injecting air at a rate of 0.5 to 1 v/vm; and collecting the produced microorganisms by centrifugation, washing the collected microorganisms twice with 0.85% physiological saline, and culturing in a sucrose solution having a Brix concentration of 60 to 77 at a temperature of 35° C. to 50° C. and a pH of 5 to 7 for 20 to 50 hours at a speed of 100 to 300 rpm.

4. A method for producing fructooligosaccharides and neofructooligosaccharides comprising:

seed culturing a *Penicillium citrinum* KCTC 10225BP having a fructosyl transferase that hydrolyzes sucrose into fructooligosaccharides of the following formula I:

Formula I

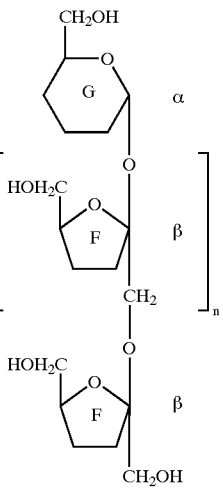

in which n is an integer of 1 to 5, G represents glucose and F represents fructose, and neofructooligosaccharides of the following formula II:

Formula II

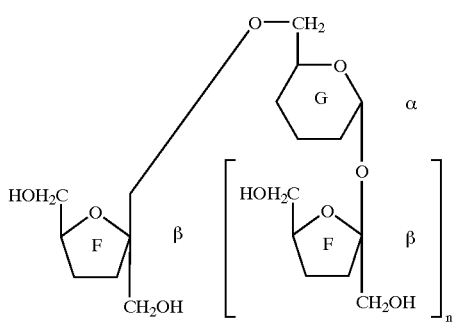

in which n is an integer of 1 to 5, G represents glucose and F represents fructose, using said fructosyl transferase;

mass-producing the seed cultured microorganism;

mixing the mass-produced microorganisms with a carrier to form beads;

packing said beads in a column; and passing a sucrose solution through said column.

5. The method of claim 4, wherein the seed culturing step is performed at 26° C. to 28° C. for 2 days while agitating at a speed of 100 to 200 rpm.

6. The method of claim 4, wherein the mass-producing step is performed at 26° C. to 28° C. for 42 to 72 hours while agitating at a speed of 200 to 600 rpm and injecting air at a rate of 0.5 to 1 v/vm.

7. The method of claim 4, wherein the carrier is one selected from a group consisting of alginate gel, photo cross-linked resin, acrylamide gel, chitosan and gelatin.

8. The method of claim 4, wherein the carrier is used at a concentration of 1 to 2%.

9. The method of claim 4, wherein the beads are produced by dropping the mixture of the microorganisms and the carrier through a needle having a diameter of 1 mm to 1 to 2% aqueous calcium chloride ($CaCl_2$) solution.

10. The method of claim 4, wherein the sucrose solution has a concentration of Brix 60 to 70.

11. The method of claim 4, wherein the sucrose solution is passed through the column at 35° C. to 55° C. and a rate of 100 to 300 mL/hour.

\* \* \* \* \*